United States Patent
Chen et al.

(10) Patent No.: US 12,053,491 B2
(45) Date of Patent: *Aug. 6, 2024

(54) BISPECIFIC OR-GATE CHIMERIC ANTIGEN RECEPTOR RESPONSIVE TO CD19 AND CD20

(71) Applicants: The Regents of the University of California, Oakland, CA (US); Seattle Children's Hospital, Seattle, WA (US)

(72) Inventors: Yvonne Y. Chen, Los Angeles, CA (US); Eugenia Zah, Los Angeles, CA (US); Michael C. Jensen, Seattle, WA (US)

(73) Assignees: The Regents of the University of California, Oakland, CA (US); Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/238,210

(22) Filed: Aug. 25, 2023

(65) Prior Publication Data

US 2024/0024359 A1 Jan. 25, 2024

Related U.S. Application Data

(63) Continuation of application No. 17/569,107, filed on Jan. 5, 2022, which is a continuation of application No. 15/535,972, filed as application No. PCT/US2015/065620 on Dec. 14, 2015, now Pat. No. 11,253,546.

(60) Provisional application No. 62/091,854, filed on Dec. 15, 2014.

(51) Int. Cl.
| | |
|---|---|
| *A61K 35/17* | (2015.01) |
| *C07K 14/705* | (2006.01) |
| *C07K 14/725* | (2006.01) |
| *C07K 16/28* | (2006.01) |
| *C07K 16/46* | (2006.01) |
| *C12N 5/0783* | (2010.01) |
| *A61K 38/00* | (2006.01) |
| *A61K 39/00* | (2006.01) |

(52) U.S. Cl.
CPC ......... *A61K 35/17* (2013.01); *C07K 14/7051* (2013.01); *C07K 14/70521* (2013.01); *C07K 14/70596* (2013.01); *C07K 16/2803* (2013.01); *C07K 16/2887* (2013.01); *C07K 16/46* (2013.01); *C12N 5/0636* (2013.01); *A61K 38/00* (2013.01); *A61K 2039/505* (2013.01); *C07K 2317/31* (2013.01); *C07K 2317/622* (2013.01); *C07K 2319/03* (2013.01); *C07K 2319/40* (2013.01); *C12N 2510/00* (2013.01)

(58) Field of Classification Search
CPC ............ C07K 16/2887; C07K 2317/31; C07K 2317/622; C07K 2319/03; C12N 5/0636; C12N 2510/00

USPC .............................................. 424/133.1, 139.1
See application file for complete search history.

(56) References Cited

U.S. PATENT DOCUMENTS

| | | |
|---|---|---|
| 4,797,368 A | 1/1989 | Carter et al. |
| 5,138,941 A | 8/1992 | Strauss |
| 5,139,941 A | 8/1992 | Muzyczka et al. |
| 5,670,373 A | 9/1997 | Kishimoto |
| 5,821,337 A | 10/1998 | Carter et al. |
| 6,074,841 A | 6/2000 | Gearing et al. |
| 6,309,842 B1 | 10/2001 | Dower et al. |
| 6,319,494 B1 | 11/2001 | Capon et al. |
| 6,410,319 B1 | 6/2002 | Raubitschek et al. |
| 7,151,169 B2 | 12/2006 | Thompson et al. |
| 7,166,423 B1 | 1/2007 | Miltenyi et al. |
| 7,276,477 B2 | 10/2007 | Osslund et al. |
| 7,446,179 B2 | 11/2008 | Jensen et al. |
| 7,479,543 B2 | 1/2009 | Tsuchiya et al. |
| 7,741,465 B1 | 6/2010 | Eshhar et al. |
| 8,012,482 B2 | 9/2011 | Adams et al. |
| 8,063,182 B1 | 11/2011 | Brockhaus et al. |
| 8,236,541 B2 | 8/2012 | Black |
| 8,399,645 B2 | 3/2013 | Campana et al. |
| 8,529,902 B2 | 9/2013 | Teeling et al. |
| 8,580,264 B2 | 11/2013 | Zhang et al. |
| 9,447,194 B2 | 9/2016 | Jensen |
| 9,464,140 B2 | 10/2016 | June et al. |
| 9,518,123 B2 | 12/2016 | June et al. |
| 9,540,445 B2 | 1/2017 | June et al. |

(Continued)

FOREIGN PATENT DOCUMENTS

| | | |
|---|---|---|
| CN | 105837693 A | 8/2016 |
| CN | 106414502 A | 2/2017 |

(Continued)

OTHER PUBLICATIONS

Martyniszyn et al (Human Gene Therapy vol. 28(12): 1147-1157; Dec. 1, 2017).*

(Continued)

*Primary Examiner* — Lynn A Bristol
(74) *Attorney, Agent, or Firm* — Foley Hoag LLP; David P. Halstead; Thi K. Dio

(57) ABSTRACT

A CD19-OR-CD20 chimeric antigen receptor (CAR) protein construct is provided. Also provided are nucleic acids encoding the CD19-OR-CD20 CAR; and methods of use, e.g. in the treatment of B cell malignancies. The CD19-OR-CD20 CAR of the invention is a bispecific CAR that can trigger T-cell activation upon detection of either CD19 or CD20 (or both). It is a single molecule that confers two-input recognition capability upon human T cells engineered to stably express this CAR.

9 Claims, 6 Drawing Sheets
Specification includes a Sequence Listing.

(56) References Cited

U.S. PATENT DOCUMENTS

| | | | |
|---|---|---|---|
| 9,765,156 B2 | 9/2017 | June et al. | |
| 9,834,590 B2 | 12/2017 | Campana et al. | |
| 9,932,412 B2 | 4/2018 | Kim et al. | |
| 10,189,903 B2 | 1/2019 | Jensen | |
| 10,253,086 B2* | 4/2019 | Bitter | A61K 45/06 |
| 10,266,592 B2 | 4/2019 | Jensen | |
| 10,442,867 B2 | 10/2019 | Orentas et al. | |
| 10,472,613 B2 | 11/2019 | Duchateau et al. | |
| 10,696,749 B2 | 6/2020 | June et al. | |
| 10,736,918 B2 | 8/2020 | Jensen et al. | |
| 10,780,118 B2 | 9/2020 | Jensen et al. | |
| 10,829,556 B2 | 11/2020 | Jensen | |
| 10,869,889 B2 | 12/2020 | Jensen et al. | |
| 10,888,581 B2 | 1/2021 | Wu et al. | |
| 11,149,076 B2* | 10/2021 | Bitter | A61K 45/06 |
| 11,160,833 B2* | 11/2021 | Chen | C07K 14/70521 |
| 11,241,485 B2* | 2/2022 | Suri | C07K 14/7155 |
| 11,253,546 B2* | 2/2022 | Chen | C07K 16/46 |
| 11,325,957 B2 | 5/2022 | Gilbert et al. | |
| 11,413,310 B2* | 8/2022 | Albertson | C07K 14/70514 |
| 11,666,642 B2* | 6/2023 | Suri | A61K 35/17 |
| | | | 424/85.2 |
| 2004/0026871 A1 | 2/2004 | Stephens et al. | |
| 2004/0254774 A1 | 12/2004 | Loh et al. | |
| 2005/0050200 A1 | 3/2005 | Mizoguchi | |
| 2006/0135517 A1 | 6/2006 | Lee et al. | |
| 2006/0251658 A1 | 11/2006 | Ledbetter et al. | |
| 2007/0142376 A1 | 6/2007 | Fleenor et al. | |
| 2007/0237779 A1 | 10/2007 | Ledbetter et al. | |
| 2009/0068158 A1 | 3/2009 | Medin et al. | |
| 2010/0330676 A1 | 12/2010 | Horowitz et al. | |
| 2011/0008364 A1 | 1/2011 | Ledbetter et al. | |
| 2011/0286980 A1 | 11/2011 | Brenner | |
| 2013/0071414 A1 | 3/2013 | Dotti et al. | |
| 2013/0280220 A1 | 10/2013 | Ahmed et al. | |
| 2014/0141000 A1 | 5/2014 | Chiu et al. | |
| 2014/0314760 A1 | 10/2014 | Rosenblum et al. | |
| 2015/0038684 A1 | 2/2015 | Jensen | |
| 2016/0280795 A1 | 9/2016 | Wang | |
| 2016/0362472 A1 | 12/2016 | Bitter et al. | |
| 2017/0137515 A1 | 5/2017 | Chang et al. | |
| 2017/0158749 A1 | 6/2017 | Cooper et al. | |
| 2017/0333480 A1 | 11/2017 | Cooper et al. | |
| 2017/0342144 A1 | 11/2017 | Wei et al. | |
| 2017/0362582 A1 | 12/2017 | Chen et al. | |
| 2017/0368098 A1 | 12/2017 | Chen et al. | |
| 2018/0022815 A1 | 1/2018 | Chang | |
| 2018/0057608 A1 | 3/2018 | Jung et al. | |
| 2018/0125892 A1 | 5/2018 | Brannetti et al. | |
| 2018/0230225 A1 | 8/2018 | Fan et al. | |
| 2018/0280433 A1 | 10/2018 | Cooper et al. | |
| 2018/0312580 A1 | 11/2018 | Chen et al. | |
| 2018/0319862 A1 | 11/2018 | Thompson et al. | |
| 2018/0362603 A1 | 12/2018 | Gilbert et al. | |
| 2019/0112380 A1* | 4/2019 | Chaudhary | A61P 35/00 |
| 2019/0169289 A1 | 6/2019 | Young et al. | |
| 2019/0202937 A1 | 7/2019 | Humphreys et al. | |
| 2020/0071421 A1 | 3/2020 | Zhou et al. | |
| 2020/0108142 A1 | 4/2020 | Wiltzius | |
| 2020/0179448 A1 | 6/2020 | Chen et al. | |
| 2020/0215108 A1 | 7/2020 | Jensen | |
| 2020/0246382 A1 | 8/2020 | Perez et al. | |
| 2020/0392200 A1 | 12/2020 | Orentas et al. | |
| 2021/0061879 A1 | 3/2021 | Williams et al. | |
| 2021/0145880 A1* | 5/2021 | Chen | C07K 16/2803 |
| 2021/0230289 A1 | 7/2021 | Chen et al. | |
| 2021/0277099 A1 | 9/2021 | Chen et al. | |
| 2021/0309740 A1 | 10/2021 | Jensen | |
| 2021/0324360 A1 | 10/2021 | Chen et al. | |
| 2022/0193136 A1* | 6/2022 | Chen | C07K 14/7051 |
| 2023/0212319 A1* | 7/2023 | Chaudhary | A61K 39/001124 |
| | | | 435/69.1 |

FOREIGN PATENT DOCUMENTS

| | | |
|---|---|---|
| CN | 107074957 A | 8/2017 |
| EP | 0610046 A2 | 8/1994 |
| EP | 1638510 A2 | 3/2006 |
| EP | 1810980 A1 | 7/2007 |
| EP | 2330193 A1 | 6/2011 |
| EP | 2445530 A1 | 5/2012 |
| EP | 2884999 A1 | 6/2015 |
| EP | 3006459 A1 | 4/2016 |
| EP | 3227323 A1 | 10/2017 |
| EP | 3240805 A1 | 11/2017 |
| EP | 3443002 A1 | 2/2019 |
| EP | 3550020 A4 | 12/2019 |
| EP | 3661964 A1 | 6/2020 |
| EP | 3687553 A1 | 8/2020 |
| EP | 3710471 A1 | 9/2020 |
| EP | 3730512 A1 | 10/2020 |
| EP | 3732205 A1 | 11/2020 |
| EP | 3824905 A1 | 5/2021 |
| JP | 2003/501348 A | 1/2003 |
| JP | 2007/515949 A | 6/2007 |
| JP | 2008/529503 A | 8/2008 |
| JP | 2013/542179 A | 11/2013 |
| JP | 2015/513394 A | 5/2015 |
| WO | WO-1992/019759 A1 | 11/1992 |
| WO | WO-1994/012520 A1 | 6/1994 |
| WO | WO-98/50432 A1 | 11/1998 |
| WO | WO-2000/66631 A1 | 11/2000 |
| WO | WO-2004/019990 A1 | 3/2004 |
| WO | WO-2005/097832 A2 | 10/2005 |
| WO | WO-2006/046661 A1 | 5/2006 |
| WO | WO-2006/086469 A2 | 8/2006 |
| WO | WO-2011/140170 A1 | 11/2011 |
| WO | WO-2012/030394 A1 | 3/2012 |
| WO | WO-2013/007052 A1 | 1/2013 |
| WO | WO-2013/123061 A1 | 8/2013 |
| WO | WO-2014/072233 A1 | 5/2014 |
| WO | WO-2014/164709 A2 | 10/2014 |
| WO | WO-2014/172584 A1 | 10/2014 |
| WO | WO-2015/121454 A1 | 8/2015 |
| WO | WO-2016/094304 A2 | 6/2016 |
| WO | WO-2016/174652 A1 | 11/2016 |
| WO | WO-2017/011342 A1 | 1/2017 |
| WO | WO-2017/075433 A1 | 5/2017 |
| WO | WO-2017/096329 A1 | 6/2017 |
| WO | WO-2017/172981 A2 | 10/2017 |
| WO | WO-2017/222593 A1 | 12/2017 |
| WO | WO-2018/102795 A2 | 6/2018 |
| WO | WO-2018/103502 A1 | 6/2018 |
| WO | WO-2019/134866 A1 | 7/2019 |
| WO | WO-2019/232444 A1 | 12/2019 |
| WO | WO-2019/237022 A1 | 12/2019 |
| WO | WO-2019/242632 A1 | 12/2019 |
| WO | WO-2020/001344 A1 | 1/2020 |
| WO | WO-2020/010235 A1 | 1/2020 |
| WO | WO-2020/033272 A1 | 2/2020 |
| WO | WO-2020/070289 A1 | 4/2020 |
| WO | WO-2020/070290 A1 | 4/2020 |
| WO | WO-2020/097193 A1 | 5/2020 |
| WO | WO-2020/113188 A2 | 6/2020 |
| WO | WO-2020/172177 A1 | 8/2020 |
| WO | WO-2020/172641 A1 | 8/2020 |
| WO | WO-2020/181164 A1 | 9/2020 |
| WO | WO-2020/216238 A1 | 10/2020 |
| WO | WO-2020/232447 A1 | 11/2020 |
| WO | WO-2020/236792 A1 | 11/2020 |
| WO | WO-2020/253393 A1 | 12/2020 |
| WO | WO-2021/003739 A1 | 1/2021 |
| WO | WO-2021/027867 A1 | 2/2021 |
| WO | WO-2021/030586 A1 | 2/2021 |

OTHER PUBLICATIONS

Schneider et al (Journal for ImmunoTherapy of Cancer (2017) 5:42; Published on-line Apr. 28, 2017).*

NCI Thesuarus-ofatumumab (p. 1; May 21, 2024).*

(56) References Cited

OTHER PUBLICATIONS

Ahmad et al., "scFv Antibody: Principles and Clinical Application," Clin Dev Immunol, 980250 (2012).

Ali, et al., "T Cells Expressing an Anti-B-Cell Maturation Antigen Chimeric Antigen Receptor Cause Remissions of Multiple Myeloma," Blood, 128:1688-1700, 2016.

Bendle et al., "Blockade of TGF-13 signaling greatly enhances the efficacy of TCR gene therapy of cancer." J. Immunol, 191 (6):3232-3239, (2013).

Berdeja, et al., "First-In-Human Multicenter Study of bb2121 Anti-BCMA CAR T-Cell Therapy for Relapsed/Refractory Multiple Myeloma: Updated Results.," Journal of Clinical Oncology, 35(15 suppl):3010-3010, 2017.

Birchenough, et al., "Equity Research: Deep Dive on Emerging Cell Therapies for Cancer," Research Report Online Wells Fargo Securities, LLC, p. 37, 5th paragraph, (Apr. 19, 2017).

Blat et al., "Suppression of murine colitis and its associated cancer by carcinoembryonic antigen-specific regulatory T cells," Mal Ther, 22:1018-1028, (2014).

Boissel et al., "Retargeting NK-92 cells bty means of CD19-and CD20-specific chemieric antigen receptors compares favorably with antibody-dependent cellular cytotoxicity," OncoImmunology, vol. 2, Issue 10, 26527 (2013).

Bollard et al., "Adapting a transforming growth factor 13-related tumor protection strategy to enhance antitumor immunity." Blood, 99(9):3179-3187,(2002).

Bond et al., "Intracellular Proteases," Annual Review of Biochemistry, vol. 56: pp. 333-364 (1987).

Brentjens et al., "CD19-targeted T cells rapidly induce molecular remissions in adults with chemotherapy-refractory acute lymphoblastic leukemia", Sci. Transl. Med., 5:177ra138, (2013).

Brudno et al., "Toxicities of chimeric antigen receptor T cells: recognition and management," Blood, vol. 127, pp. 3321-3330 (2016).

Brunstein et al., "Umbilical cord blood-derived T regulatory cells to prevent GVHD: kinetics, toxicity profile, and clinical effect," Blood, vol. 127, pp. 1044-1051, (2016).

Brusko et al., "Human antigen-specific regulatory T cells generated by T cell receptor gene transfer", PLoS One, 5:e11726, (2010).

Budde et al., "Combining a CD20 chimeric antigen receptor and an inducible caspase 9 suicide switch to improve the efficacy and safety of T cell adoptive immunotherapy for lymphoma," PloS One, vol. 8, issue 12, e82742, (2013).

Carpenter et al., "B-cell Maturation Antigen Is a Promising Target for Adoptive Tcell Therapy of Multiple Myeloma," Clinical Cancer Research, vol. 19 No. 8, pp. 2048-2060, (2013).

Chang et al., "Rewiring T-cell responses to soluble factors with chimeric antigen receptors," Nat. Chem. Biol., vol. 14, No. 3, pp. 317-324 (2018).

Chen et al., "Fusion protein linkers: Property, design and functionality", Advanced Drug Delivery Reviews, vol. 65, pp. 1357-1369. (2003).

Chen et al., "A Unique Substrate Recognition Profile for Matrix Metalloproteinase-2," The Journal of Biological Chemistry, vol. 277, No. 6, pp. 4485-4491, (2002).

Chen, et al., "A Compound Chimeric Antigen Receptor Strategy For Targeting Multiple Myyeloma." Leukemia, vol. 32, No. 2, pp. 402-412 (2018).

Chmielewski, et al., "IL-12 Release by Engineered T Cells Expressing Chimeric Antigen Receptors Can Effectively Muster an Antigen-Independent Macrophage Response on Tumor Cells That Have Shut Down Tumor Antigen Expression." Cancer Research, vol. 71, No. 17, pp. 5697-5706 (2011).

Chu et al., "CS1-Specific Chimeric Antigen Receptor (CAR)-Engineered Natural Killer Cells Enhance In Vitro and In Vivo Antitumor Activity Against Human Multiple Myeloma," Leukemia vol. 28, pp. 917-927, (2014).

Chu, "Genetic Modification of T Cells Redirected toward CS1 Enhances Eradication of Myeloma Cells," Clinical Cancer Research, vol. 20, No. 15, pp. 3989-4000 (2014).

Cohen et al., "B-Cell Maturation Antigen (BCMA) Specific Chimeric Antigen Receptor T Cells (CART-BCMA) for Multiple Myeloma (MM): Initial Safety and Efficacy From a Phase I Study," Blood, vol. 128, p. 1147 (2016).

Cooper et al., "T-cell clones can be rendered specific for CD19: toward the selective augmentation of the graft-versus-B-lineage leukemia effect" Blood, vol. 101, No. 4, pp. 1637-1644 (2003).

Corrigan-Curay et al., "T-Cell Immunotherapy: Looking forward." Mal. Ther, vol. 22, pp. 1564-1574 (2014).

Dalken et al., "Targeted Induction of Apoptosis by Chimeric Granzyme B Fusion Proteins Carrying Antibody and Growth Factor Domains for Cell Recognition," Cell Death Differentiation, vol. 13, pp. 576-585. (2006).

Davila et al., "Efficacy and toxicity management of 19-28z CAR T cell therapy in B cell acute lymphoblastic leukemia.", Sci. Transl. Med., 6:224ra225, (2014).

Dotti et al., "Design and development of therapies using chimeric antigen receptor-expressing T-cells", Immunological Reviews, vol. 257, pp. 107-126, (2014).

Duebner et al., "Reprogramming Control of an Allosteric Signaling Switch Through Modular Recombination," Science, vol. 301, No. 5641, pp. 1904-1908. (2003).

Duffy, "Proteases as Prognostic Markers in Cancer," Clinical Cancer Research, vol. 2: pp. 613-618, (1996).

Dull et al., "A Third-Generataion Lentivirus Vector with a Conditional Packaging System," J.Virol, vol. 72, Issue 11, pp. 8463-8471 (1998).

Ellebrecht et al., "Reengineering chimeric antigen receptor T cells for targeted therapy of autoimmune disease," Science, p. 353, 179-184 (2016).

Extended European Search Report Issued in Corresponding European Application 15870819.8, dated Apr. 13, 2018.

Extended European Search Report Issued in Corresponding European Patent Application No. 16860930.3, dated Oct. 10, 2019.

Extended Search Report issued in Corresponding European Application No. 19/819799.8, dated Jan. 25, 2022.

Foster et al., "Antitumor activity of EBC-specific T lymphocytes transduced with a dominant negative TGF-13 receptor," J. Immunother., 31 (5):500-505 (2008).

Gogishvili et al., "SLAMF7-CAR T Cells Eliminate Myeloma and Confer Selective Fratricide of SLAMF7 + Normal Lymphocytes," Blood, vol. 130: pp. 2838-2847 (2017).

Gorelik et al., "Immune-mediated eradication of tumors through the blockade of transforming growth factor-13 signaling in T cells" Nat. Med., vol. 7, pp. 1118-1122 (2001).

Hay, "SUMO-Specific Proteases: A Twist in the Tail," Trends in Cell Biology, vol. 17 No. 8, pp. 370-376, (2007).

Hillerdal et al., "Chimeric antigen receptor-engineered T cells for the treatment of metastatic prostate cancer," BioDrugs, vol. 29, pp. 75-89 (2015).

Ho et al., "Covert Cancer Therapeutics: Engineering T Cells to Interrogate Intracellular Tumor Antigens," 2015 AICHE Annual Meeting, (Nov. 12, 2015).

Ho et al., "Modularly Constructed Synthetic Granzyme B Molecule Enables Interrogation of Intracellular Proteases for Targeted Cytotoxicity ," ACS Synthetic Biology, vol. 6, pp. 1484-1495. (2017).

Homach et al., "An anti-CD30 chimeric receptor that mediates CD3-zeta-independent T-cell activation against Hodgkin's lymphoma cells in the presence of soluble CD30."Cancer Research, American Association for Cancer Research, vol. 58, No. 6, pp. 1116-1119 (1998).

International Preliminary Report on Patentability Issued in Corresponding PCT Patent Application No. PCT/US2019/036731, dated Dec. 15, 2020.

International Search Report and Written Opinion Issued in Corresponding PCT Application No. PCT/US2015/065623, dated Apr. 19, 2016.

International Search Report and Written Opinion Issued in Corresponding PCT Patent Application No. PCT/US2019/036731, dated Dec. 27, 2019.

International Search Report and Written Opinion Issued in International Application No. PCT/US2015/065620, dated Mar. 28, 2016.

(56) References Cited

OTHER PUBLICATIONS

International Search Report and Written Opinion issued in International Application No. PCT/US2016/059444, dated Feb. 14, 2017.
International Search Report and Written Opinion issued in International Patent Application No. PCT/IB2017/055281, dated Mar. 8, 2018.
Kalos et al., "T cells with chimeric antigen receptors have potent antitumor effects and can establish memory in patients with advanced leukemia," Sci. Transl. Med., vol. 3, No. 95 (2011).
Kelchtermans et al., "Activated CD4+CD25+ regulatory T cells inhibit osteoclastogenesis and collagen-induced arthritis", Ann. Rheum. Dis., 68:744-750, (2009).
Kessenbrock, et al., "Matrix Metalloproteinases: Regulators of the Tumor Microenvironment," Cell, vol. 141, No. 1, pp. 52-67, (2010).
Kochenderfer et al., "B-cell depletion and remissions of malignancy along with cytokine-associated toxicity in a clinical trial of anti-CD19 chimeric-antigen-receptor-transduced T cells", Blood, vol. 119, pp. 2709-2720 (2012).
Kowalik et al., "CD28 Costimulation Provided through a CD19-Specific Chimeric Antigen Receptor Enhances In vivo Persistence and Antitumor Efficacy of Adoptively Transferred T Cells" Cancer Res, vol. 66, No. 22, pp. 10995-11004.(2006).
Lanitis et al., "Redirected Antitumor Activity of Primary Human Lymphocytes Transduced With a Fully Human Anti mesothelin Chimeric Receptor", Molecular Therapy, vol. 20, No. 3, pp. 633-643 (2012).
Le Gall et al., "Effect of linker sequences between the antibody variable domains on the formation, stability and biological activity of a bispecific tandem diabody" Protein Engineering Design and Selection, vol. 17, No. 4, pp. 357-366. (2004).
Le Gall et al., "Immunosuppressive properties of anti-CD3 single-chain Fv and diabody" Journal of Immunological Methods, vol. 285, pp. 111-127 (2004).
Lee et al., "An APRIL-Based Chimeric Antigen Receptor for Dual Targeting of BCMA and TACI in Multiple Myeloma," Blood, vol. 131, pp. 746-758, (2018).
Lee et al., "Current concepts in the diagnosis and management of cytokine release syndrome," Blood, vol. 124, pp. 188-195(2014).
Lopez-Otin et al., "Emerging Roles of Proteases in Tumour Suppression," Nature, vol. 7: pp. 800-808, (2007).
Ma et al. "Carcinoembryonic antigen-immunoglobulin Fc fusion protein (CEA-Fc) for identification and activation of anti-CEA im-munoglobulin-T-cell receptor-modified T cells, representative of a new class of Ig fusion proteins", Cancer Gene Therapy, vol. 11, pp. 297-306 (2004).
Malakhov et al., SUMO Fusions and SUMO-Specific Protease for Efficient Expression and Purification of Proteins, Journal of Structural and Functional Genomics, vol. 5, No. 1-2, pp. 75-86, (2004).
Maude et al., "Chimeric Antigen Receptor T Cells for Sustained Remissions in Leukemia" N Engl J Med, vol. 371, No. 16, pp. 1507-1517. (2014).
Maude et al., "Managing Cytokine Release Syndrome Associated with Novel T Cell-Engaging Therapies," The Cancer Journal, vol. 20, No. 2, pp. 119-122, (2014).
Morgan et al., "Effective treatment of collagen-induced arthritis by adoptive transfer of CD25+ regulatory T cells," Arthritis Rheum, vol. 52: pp. 2212-2221 (2005).
Myasoedova et al., "Is the incidence of rheumatoid arthritis rising ?: results from Olmsted County, Minnesota, 1955-2007", Arthritis Rheum, vol. 62, pp. 1576-1582, (2010).
Nakamura et al., "TGF-beta 1 plays an important role in the mechanism of CD4+CD25+ regulatory T cell activity in both humans and mice," J Immunol, vol. 164, pp. 183-190 (2004).
Nicholson et al., "Construction and characterisation of a functional CD19 specific single chain Fv fragment for immunotherapy of B lineage leukaemia and lymphoma" Molecular Immunology, vol. 34, No. 16-17, pp. 1157-1165 (1997).
Office Action and Search Report dated Oct. 12, 2022 in Chinese Application No. 201980053239.6.

Office Action Issued in Corresponding Japanese Patent Application No. 2018-522004, dated Oct. 12, 2020.
Office Action Issued in Corresponding U.S. Appl. No. 15/772,403, dated Apr. 9, 2020.
Office Action Issued in Corresponding U.S. Appl. No. 15/772,403, dated Oct. 8, 2020.
Partial Search Report issued in Corresponding European Patent Application No. 16860930, dated Jun. 26, 2019 .
Pastan et al., "Immunotoxin Treatment of Cancer," Annual Review of Medicine, vol. 58, pp. 221-223 (2007).
Patel et al., "Cancer CARtography: Charting Out a New Approach to Cancer Immunotherapy," vol. 6, No. 6, pp. 675-678, (2014).
Porter et al., "Chimeric antigen receptor-modified T cells in chronic lymphoid leukemia," N. Engl. J. Med., vol. 365: pp. 725-733 (2011).
Qin et al., "Supplemental Information. Preclinical Development of Bivalent Chimeric Antigen Receptors Targeting Both CD19 and CD22", Molecular Therapy: Oncolytics, vol. 11, pp. 127-137 (2018).
Qin et al., "Preclinical Development of Bivalent Chimeric Antigen Receptors Targeting Both CD19 and CD22", Molecular Therapy: Oncolytics, vol. 11, pp. 127-137. (2018).
Quatromoni et al., "T cell receptor (TCR)-transgenic CD8 lymphocytes rendered insensitive to transforming growth factor beta (TGFl3) signaling mediate superior tumor regression in an animal model of adoptive cell therapy" J. Transl. Med., vol. 10, No. 127, (2012).
Ramadoss et al., "An anti-B cell maturation antigen bispecific antibody for multiple myeloma." J Am Chem Soc; pp. 5288-5291 (2015).
Rosenberg, "Finding suitable targets is the major obstacle to cancer gene therapy", Cancer Gene Ther., vol. 21, pp. 45-47 (2017).
Rosenzweig et al., "Preclinical Data Support Leveraging CS1 Chimeric Antigen Receptor T-Cell Therapy For Systemic Light Chain Amyloidosis," Cytotherapy, vol. 19, No. 7 pp. 861-866, (2017).
Stahnke et al., "Granzyme B-H22 (scFv), a Human Immunotoxin Targeting CD64 in Acute Myeloid Leukemia in Monocytic Subtypes," Molecular Cancer Therapeutics, vol. 7, No. 9, pp. 2924-2932. (2008).
Stone et al., "A sensitivity scale for targeting T cells with chimeric antigen receptors (CARs) and bispecific T-cell engagers (BITEs)" Oncoimmunology, vol. 1, No. 6, pp. 863-873 (2012).
Suarez, et al., "Chimeric Antigen Receptor T Cells Secreting Anti-PD-L1 Antibodies More Effectively Regress Renal Cell Carcinoma in a Humanized Mouse Model," Oncotarget, vol. 7, No. 23, pp. 34341-34355, (2016).
Summons to attend oral proceedings pursuant to Rule 115(1) EPC issued in European Application No. 16860930.3 dated Oct. 13, 2021.
Supplementary European Search Report issued in European Application No. 15870818, dated Apr. 10, 2018.
Szymczak-Workman et al., "Design and construction of 2A peptide-linked multicistronic vectors," Cold Spring Harb Protoc, vol. 2012, No. 2, pp. 199-204 (2012).
Tang et al., "Regulatory T-cell therapy in transplantation: moving to the clinic", Cold Spring Harb Perspect Med., 3:a015552, (2013).
Thornberry, et al., "A Combinatorial Approach Defines Specificities of Members of the Caspase Family and Granzyme B," The Journal of Biological Chemistry, vol. 272, No. 29, pp. 17907-17911, (1997).
Thornton et al., "Suppressor effector function of CD4+CD25+ immunoregulatory T cells is antigen nonspecific", J Immunol, vol. 164, pp. 183-190, (2000).
Wang et al., "Lenalidomide Enhances the Function of CS1 Chimeric Antigen Receptor-Redirected T Cells Against Multiple Myeloma," Clinical Cancer Research, vol. 24, No. 1, pp. 106-119, (2018).
Westwood et al., "The Lewis-Y Carbohydrate Antigen is Expressed by Many Human Tumors and Can Serve as a Target for Genetically Redirected T cells Despite the Presence of Soluble Antigen in Serum." Journal of Immunotherapy, vol. 32, No. 3, pp. 292-301 (2009).
Widdifield et al., "The epidemiology of rheumatoid arthritis in Ontario, Canada." Arthritis Rheumatol, vol. 66, pp. 786-793 (2014).

(56) References Cited

OTHER PUBLICATIONS

Wright et al., "Adoptive therapy with redirected primary regulatory T cells results in antigen-specific suppression of arthritis," Proc. Natl. Acad. Sci. vol 106, No. 45, pp. 19078-19083 (2009).
Wright et al., "Regulatory T-cell adoptive immunotherapy: potential for treatment of autoimmunity", Expert Rev. Clin. Immunol., vol. 7, pp. 213-225, (2011).
Wu et al., "FOXP3 controls regulatory T cell function through cooperation with NFAT", Cell, vol. 126, pp. 375-387, (2006).
Wyatt, et al., "Human Telomerase Reverse Transcriptase (hTERT) 0169 Is Essential for Telomerase Function In Vitro and In Vivo," PLoS One, vol. 4, No. 9, pp. 1-14. (2009).
Yingling et al., "Development of TGF-l3 signalling inhibitors for cancer therapy" Nat. Rev. Drug Discov., vol. 3, pp. 1011-1022 (2004).
Zah et al., "T cells expressing CD19/CD20 bi-specific chimeric antigen receptors prevent antigen escape by malignant B cells" Cancer Immunol Res , vol. 4, No. 6, pp. 498-641. (2016).
Zah et al., Systematically optimized BCMNCS1 bispecific CAR-T cells robustly control heterogeneous multiple myeloma; Nature Communications, vol. 11, No. 1 (2020).
Zhang et al., "Adoptive Transfer of Tumor-Reactive Transforming Growth Factor-l3-Insensitive CDS+ T Cells" Cancer Res. vol. 65, No. 5, pp. 1761-1769. (2005).
Zhang et al., "Engineering CAR-T cells." Biomarker Research, Biomed Central Ltd, London, UK, vol. 5, No. 1, pp. 1-6.(2017).
Zhang et al., "Inhibition of TGF-l3 signaling in genetically engineered tumor antigen-reactive T cells significantly enhances tumor treatment efficacy," Gene Ther, vol. 20, pp. 575-580, (2012).
Zhao, et al., "Secreted Antibody/Granzyme B Fusion Protein Stimulates Selective Killing of HER2-overexpressing Tumor Cells," The Journal of Biological Chemistry, vol. 279, No. 20, pp. 21343-21348. (2004).
Zhi-Zhang et al. "Soluble and Membrane-Bound TGF [beta]-Mediated Regulation of Intratumoral T Cell Differentiation and Function in B-Cell Non-Hodgkin Lymphoma", PLoS One, vol. 8, No. 3, p. e59456 (2013).
Bendle et al., "Blockade of TGF-beta signaling greatly enhances the efficacy of TCR gene therapy of cancer." J. Immunol, 191 6:3232-3239, (2013).
Blat et al., "Suppression of murine colitis and its associated cancer by carcinoembryonic antigen-specific regulator T cells," Mol Ther, 22:1018-1028, (2014).
Boissel et al., "Retargeting NK-92 cells bty means of CD19-and CD20-specific chemieric antigen receptors compares favorably with antibody-dependent cellular cytotoxicity," OncoImmunology, vol. 2, Issue 10, e26527 (2013).
Bollard et al., "Adapting a transforming growth factor beta-related tumor protection strategy to enhance antitumor immunity." Blood, 99(9):3179-3187,(2002).
Cohen et al., "B cell maturation antigen-specific CAR T cells are clinically active in multiple myeloma." The Journal of Clinical Investigation 129.6 (2019):2210-2221.
Communication pursuant to 94(3) EPC for EP Application No. 15870818 dated Aug. 4, 2020.
Communication pursuant to 94(3) EPC for EP Application No. 15870818 dated Feb. 10, 2022.
Communication pursuant to 94(3) EPC for EP Application No. 15870818 dated Jul. 4, 2019.
Communication pursuant to 94(3) EPC for EP Application No. 15870818 dated Jun. 27, 2023.
Corrigan-Curay et al., "T-Cell Immunotherapy: Looking forward." Mol. Ther, vol. 22, pp. 1564-1574 (2014).
Du et al., "Structure of the Fab fragment of therapeutic antibody Ofatumumab provides insights into the recognition mechanism with CD20." Molecular Immunology 46 (2009):2419-2423.
Examiner Resort for CA Application No. 3008162 dated Nov. 25, 2022.
Examiner Report for CA Application No. 3008162 dated Dec. 14, 2021.

Extended European Search Report for EP Application No. 168609303, dated Oct. 9, 2019.
Extended European Search Report for EP Application No. 17845645.5, dated Mar. 24, 2020.
Extended European Search Report for EP Application No. 19819799.8, dated Jan. 25, 2022.
Final Office Action for U.S. Appl. No. 15/535,972, dated Mar. 11, 2020.
Foster et al., "Antitumor activity of EBC-specific T lymphocytes transduced with a dominant negative TGF-beta receptor," J. Immunotherapy, 31 (5):500-505 (2008).
GenBank Accession No. AMZ04824.1 ; Submitted: Mar. 29, 2016; Publication Date: Apr. 24, 2016.
GenBank Accession No. KX000905.1 referencing AMZ04818.1; Submitted: Mar. 29, 2016; Publication Date: Apr. 24, 2016.
GenBank Accession No. KX000911 referencing AMZ04824; Submitted: Mar. 29, 2016; Publication Date: Apr. 24, 2016.
Gorelik et al., "Immune-mediated eradication of tumors through the blockade of transforming growth factor-beta signaling in T cells" Nat. Med., vol. 7, pp. 1118-1122 (2001).
Kalos et al., "T cells with chimeric antigen receptors have potent antitumor effects and can establish memory in patients with advanced leukemia," Sci. Transl. Med., vol 3, No. 95, p. 95ra73 (2011).
Kelchtermans et al., "Defective CD4+ CD25+ regulatory T cell functioning in collagen-induced arthritis: an important factor in pathogenesis, counter-regulated by endogenous IFN-gamma." Arthritis Res Ther 7 (2005): R402-R415.
Non-Final Office Action for U.S. Appl. No. 15/535,972, dated Feb. 8, 2021.
Non-Final Office Action for U.S. Appl. No. 15/535,972, dated Sep. 13, 2019.
Notice of Allowance for U.S. Appl. No. 15/535,972, dated Oct. 14, 2021.
Notice of Allowance for U.S. Appl. No. 17/028,701, dated Jul. 2, 2021.
Patel et al., "Cancer CARtography: Charting Out a New Approach to Cancer Immunotherapy," Immunotherapy, vol. 6, No. 6, pp. 675-678, (2014).
Quatromoni et al., "T cell receptor (TCR)-transgenic CD8 lymphocytes rendered insensitive to transforming growth factor beta (TGF beta) signaling mediate superior tumor regression in an animal model of ado-tive cell therapy" J. Transl. Med., vol 10, No. 127, (2012).
RCSB Protein Data Bank, Accession Code: 3GIZ (May 26, 2009).
Requirement for Restriction for U.S. Appl. No. 15/772,403, dated Jan. 16, 2020.
Requirement for Restriction for U.S. Appl. No. 17/028,701, dated Apr. 16, 2021.
Shah et al., "A Phase 1 Study with Point-of-Care Manufacturing of Dual Targeted, Tandem Anti-CD19, Anti-CD20 Chimeric Antigen Receptor Modified T (CAR-T) Cells for Relapsed, Refractory, Non-Hodokin Lymphoma." ASH, 2018 :4193.
Shah et al., "Clinical Results of a First-in-Human Phase 1 Study of Point-of-Care Manufactured Bispecific Anti-CD19, Anti-CD20 Chimeric Antigen Receptor Modified T (CAR-20.19-T) Cells for Relapsed, Refractory, Non-Hodgkin Lymphoma (NHL)." Biology of Blood and Marrow Transplantation, Abstract, 2019:80.
Tong et al., "Optimized tandem CD19/CD20 CAR-engineered T cells in refractory/relapsed B-cell lymphoma." Blood, The Journal of the American Society of Hematology 136(14) (2020): 1632-1644.
Wyatt, et al., "Human Telomerase Reverse Transcriptase (hTERT) Q169 Is Essential for Telomerase Function In Vitro and In Vivo," PLoS One, vol 4, No. 9, pp. 1-14. (2009).
Yang et al., "Soluble and Membrane-Bound TGF [beta]-Mediated Regulation of Intratumoral T Cell Differentiation and Function in B-Cell Non-Hodgkin Lymphoma", PLoS ONE, vol. 8, No. 3, p. e59456 (2013).
Yingling et al., "Development of TGF-beta signalling inhibitors for cancer therapy" Nat. Rev. Drug Discov., vol. 3, pp. 1011-1022 (2004).

(56) References Cited

OTHER PUBLICATIONS

Zhang et al., "Adoptive Transfer of Tumor-Reactive Transforming Growth Factor-beta-Insensitive CD8+ T Cells" Cancer Res. vol. 65, No. 5, pp. 1761-1769. (2005).

Zhang et al., "Inhibition of TGF-beta signaling in genetically engineered tumor antigen-reactive T cells significantly enhances tumor treatment efficacy," Gene Ther, vol 20, pp. 575-580, (2012).

Zhang et al., "Long-term activity of tandem CD19/CD20 CAR therapy in refractory/relapsed B-cell lymphoma: a single-arm, phase 1-2 trial." Leukemia 36 (2022): 189-196.

U.S. Appl. No. 15/535,972, filed Jun. 14, 2017, 20170368098, U.S. Pat. No. 11,253,546, Granted.

U.S. Appl. No. 17/028,701, filed Sep. 22, 2020, 20210145880, U.S. Pat. No. 11,160,833, Granted.

U.S. Appl. No. 17/569,107, filed Jan. 5, 2022, 20220193136, Published.

U.S. Appl. No. 18/444,026, filed Feb. 16, 2024, 20240024359, Pending.

\* cited by examiner

Signal Seq | CD20 scFv | Linker | CD19 scFv | Spacer | CD28tm | 4-1BB | CD3ζ | T2A | EGFRt

FIG. 1

SEQUENCE LISTING

```
Sequence total quantity: 19
SEQ ID NO: 1         moltype = AA  length = 5
FEATURE              Location/Qualifiers
```

-continued

```
source                          1..5
                                mol_type = protein
                                organism = Homo sapiens
SEQUENCE: 1
EAAAK                                                                     5

SEQ ID NO: 2                    moltype = AA  length = 20
FEATURE                         Location/Qualifiers
source                          1..20
                                mol_type = protein
                                organism = Homo sapiens
SEQUENCE: 2
METDTLLLWV LLLWVPGSTG                                                    20

SEQ ID NO: 3                    moltype = AA  length = 246
FEATURE                         Location/Qualifiers
source                          1..246
                                mol_type = protein
                                organism = Homo sapiens
SEQUENCE: 3
DIVLTQSPAI LSASPGEKVT MTCRASSSVN YMDWYQKKPG SSPKPWIYAT SNLASGVPAR         60
FSGSGSGTSY SLTISRVEAE DAATYYCQQW SFNPPTFGGG TKLEIKGSTS GGGSGGGSGG        120
GGSSEVQLQQ SGAELVKPGA SVKMSCKASG YTFTSYNMHW VKQTPGQGLE WIGAIYPGNG        180
DTSYNQKFKG KATLTADKSS STAYMQLSSL TSEDSADYYC ARSNYYGSSY WFFDVWGAGT        240
TVTVSS                                                                  246

SEQ ID NO: 4                    moltype = AA  length = 245
FEATURE                         Location/Qualifiers
source                          1..245
                                mol_type = protein
                                organism = Homo sapiens
SEQUENCE: 4
DIQMTQTTSS LSASLGDRVT ISCRASQDIS KYLNWYQQKP DGTVKLLIYH TSRLHSGVPS         60
RFSGSGSGTD YSLTISNLEQ EDIATYFCQQ GNTLPYTFGG GTKLEITGST SGSGKPGSGE        120
GSTKGEVKLQ ESGPGLVAPS QSLSVTCTVS GVSLPDYGVS WIRQPPRKGL EWLGVIWGSE        180
TTYYNSALKS RLTIIKDNSK SQVFLKMNSL QTDDTAIYYC AKHYYGGSY AMDYWGQGTS         240
VTVSS                                                                   245

SEQ ID NO: 5                    moltype = AA  length = 12
FEATURE                         Location/Qualifiers
source                          1..12
                                mol_type = protein
                                organism = Homo sapiens
SEQUENCE: 5
ESKYGPPCPP CP                                                            12

SEQ ID NO: 6                    moltype = AA  length = 28
FEATURE                         Location/Qualifiers
source                          1..28
                                mol_type = protein
                                organism = Homo sapiens
SEQUENCE: 6
MFWVLVVVGG VLACYSLLVT VAFIIFWV                                           28

SEQ ID NO: 7                    moltype = AA  length = 41
FEATURE                         Location/Qualifiers
source                          1..41
                                mol_type = protein
                                organism = Homo sapiens
SEQUENCE: 7
RSKRSRGGHS DYMNMTPRRP GPTRKHYQPY APPRDFAAYR S                            41

SEQ ID NO: 8                    moltype = AA  length = 42
FEATURE                         Location/Qualifiers
source                          1..42
                                mol_type = protein
                                organism = Homo sapiens
SEQUENCE: 8
KRGRKKLLYI FKQPFMRPVQ TTQEEDGCSC RFPEEEEGGC EL                           42

SEQ ID NO: 9                    moltype = AA  length = 112
FEATURE                         Location/Qualifiers
source                          1..112
                                mol_type = protein
                                organism = Homo sapiens
SEQUENCE: 9
RVKFSRSADA PAYQQGQNQL YNELNLGRRE EYDVLDKRRG RDPEMGGKPR RKNPQEGLYN         60
ELQKDKMAEA YSEIGMKGER RRGKGHDGLY QGLSTATKDT YDALHMQALP PR                112
```

-continued

```
SEQ ID NO: 10              moltype = AA   length = 24
FEATURE                    Location/Qualifiers
source                     1..24
                           mol_type = protein
                           organism = Homo sapiens
SEQUENCE: 10
LEGGGEGRGS LLTCGDVEEN PGPR                                          24

SEQ ID NO: 11              moltype = AA   length = 110
FEATURE                    Location/Qualifiers
source                     1..110
                           mol_type = protein
                           organism = Homo sapiens
SEQUENCE: 11
APEFLGGPSV FLFPPKPKDT LMISRTPEVT CVVVDVSQED PEVQFNWYVD GVEVHNAKTK    60
PREEQFNSTY RVVSVLTVLH QDWLNGKEYK CKVSNKGLPS SIEKTISKAK              110

SEQ ID NO: 12              moltype = AA   length = 107
FEATURE                    Location/Qualifiers
source                     1..107
                           mol_type = protein
                           organism = Homo sapiens
SEQUENCE: 12
GQPREPQVYT LPPSQEEMTK NQVSLTCLVK GFYPSDIAVE WESNGQPENN YKTTPPVLDS    60
DGSFFLYSRL TVDKSRWQEG NVFSCSVMHE ALHNHYTQKS LSLSLGK                 107

SEQ ID NO: 13              moltype = AA   length = 357
FEATURE                    Location/Qualifiers
source                     1..357
                           mol_type = protein
                           organism = Homo sapiens
SEQUENCE: 13
MLLLVTSLLL CELPHPAFLL IPRKVCNGIG IGEFKDSLSI NATNIKHFKN CTSISGDLHI    60
LPVAFRGDSF THTPPLDPQE LDILKTVKEI TGFLLIQAWP ENRTDLHAFE NLEIIRGRTK   120
QHGQFSLAVV SLNITSLGLR SLKEISDGDV IISGNKNLCY ANTINWKKLF GTSGQKTKII   180
SNRGENSCKA TGQVCHALCS PEGCWGPEPR DCVSCRNVSR GRECVDKCNL LEGEPREFVE   240
NSECIQCHPE CLPQAMNITC TGRGPDNCIQ CAHYIDGPHC VKTCPAGVMG ENNTLVWKYA   300
DAGHVCHLCH PNCTYGCTGP GLEGCPTNGP KIPSIATGMV GALLLLLVVA LGIGLFM      357

SEQ ID NO: 14              moltype = AA   length = 30
FEATURE                    Location/Qualifiers
source                     1..30
                           mol_type = protein
                           organism = synthetic construct
VARIANT                    6..30
                           note = EAAAK repeats may be deleted
SEQUENCE: 14
EAAAKEAAAK EAAAKEAAAK EAAAKEAAAK                                     30

SEQ ID NO: 15              moltype = AA   length = 5
FEATURE                    Location/Qualifiers
source                     1..5
                           mol_type = protein
                           organism = synthetic construct
SEQUENCE: 15
GGGGS                                                                5

SEQ ID NO: 16              moltype = AA   length = 15
FEATURE                    Location/Qualifiers
source                     1..15
                           mol_type = protein
                           organism = synthetic construct
SEQUENCE: 16
GGGGSGGGGS GGGGS                                                    15

SEQ ID NO: 17              moltype = AA   length = 15
FEATURE                    Location/Qualifiers
source                     1..15
                           mol_type = protein
                           organism = synthetic construct
SEQUENCE: 17
EAAAKEAAAK EAAAK                                                    15

SEQ ID NO: 18              moltype = AA   length = 50
FEATURE                    Location/Qualifiers
source                     1..50
                           mol_type = protein
                           organism = synthetic construct
VARIANT                    6..50
```

```
                        note = EAAAK repeats may be deleted
SEQUENCE: 18
EAAAKEAAAK EAAAKEAAAK EAAAKEAAAK EAAAKEAAAK EAAAKEAAAK                      50

SEQ ID NO: 19          moltype = AA   length = 20
FEATURE                Location/Qualifiers
source                 1..20
                       mol_type = protein
                       organism = synthetic construct
SEQUENCE: 19
GGGGSGGGGS GGGGSGGGGS                                                       20
```

BISPECIFIC OR-GATE CHIMERIC ANTIGEN RECEPTOR RESPONSIVE TO CD19 AND CD20

CROSS REFERENCE TO RELATED APPLICATIONS

This application is a continuation of U.S. patent application Ser. No. 17/569,107 filed on Jan. 5, 2022, which is a continuation of U.S. patent application Ser. No. 15/535,972 filed on Jun. 14, 2017, now U.S. Pat. No. 11,253,546, which is a national phase application under 35 U.S.C. § 371 of International Application No. PCT/US2015/065620, filed Dec. 14, 2015, which claims the benefit of U.S. Provisional Application No. 62/091,854, filed Dec. 15, 2014. The contents of these applications are incorporated into the present application by reference. U.S. patent application Ser. No. 17/028,701, filed Sep. 22, 2020, now U.S. Pat. No. 11,160,833, is a related divisional application of U.S. patent application Ser. No. 15/535,972, filed Jun. 14, 2017, now U.S. Pat. No. 11,253,546.

GOVERNMENT SUPPORT

This invention was made with Government support under OD012133, awarded by the National Institutes of Health. The Government has certain rights in the invention. This work was supported by the U.S. Department of Veterans Affairs, and the Federal Government has certain rights in the invention.

SEQUENCE LISTING

This application contains a Sequence Listing in computer readable form. The computer readable form is incorporated herein by reference. Said XML copy, created on Jan. 22, 2024, is named UCH-37604_SL.xml and is 19,543 bytes in size.

BACKGROUND OF THE INVENTION

Chimeric antigen receptors (CARs) are artificial molecules that redirect the specificity of T cells to predetermined antigens. These receptors are frequently used to graft the specificity of a monoclonal antibody onto a T cell; with transfer of their coding sequence facilitated by retroviral or lentiviral vectors. Using adoptive transfer, autologous T cells can be genetically modified ex vivo to express a CAR specific for a cancer cell of interest. The T cells, which can then recognize and kill the cancer cells, are reintroduced into the patient. Phase I clinical studies of this approach have shown efficacy.

The most common form of CARs are fusions of single-chain variable fragments (scFv) derived from monoclonal antibodies, fused to CD3-zeta signaling domain, which contains 3 ITAMs. CD3-zeta may not provide a fully competent activation signal and additional co-stimulatory signaling is needed. For example, chimeric CD28 and OX40 can be used with CD3-Zeta to transmit a proliferative/survival signal, or all three can be used together. Such molecules result in the transmission of a zeta signal in response to recognition by the scFv of its target.

Multiple clinical trials have reported remarkable therapeutic efficacy of anti-CD19 CAR-modified T cells against both acute and chronic B-cell malignancies. However, multiple cases have also been reported of patients relapsing with the emergence of CD19-negative leukemia or lymphoma (Maude et al. 2014). This problem of antigen escape, i.e., tumor cells evading treatment by losing the antigen targeted by the T-cell therapeutic, is addressed by this invention.

SUMMARY OF THE INVENTION

CD20 and CD19 are both pan-B-cell markers present on the vast majority of malignant B cells. An OR-gate CAR that triggers tumor killing as long as either CD20 or CD19 is present reduces the probability of antigen escape, by requiring that tumor cells lose both antigens to escape targeting, an event that happens with a significantly lower probability than single-antigen mutations. Therefore, this invention has a strong competitive advantage compared to the conventional, single-input anti-CD19 CAR T-cell therapy.

A CD19-OR-CD20 chimeric antigen receptor (CAR) protein construct is provided. Also provided are nucleic acids encoding the CD19-OR-CD20 CAR; and methods of use, e.g. in the treatment of B cell malignancies. The CD19-OR-CD20 CAR of the invention is a bispecific CAR that can trigger T-cell activation upon detection of either CD19 or CD20 (or both). It is a single molecule that confers two-input recognition capability upon human T cells engineered to stably express this CAR. The CD19-OR-CD20 CAR consists of the following (from N- to C-terminus): signal sequence; anti CD20 scFv; linker; anti-CD19 scFv; spacer domain; transmembrane domain; zero, one, or more cytoplasmic co-stimulatory signaling domains; CD3 zeta signaling domain. In some embodiments the spacer domain is an immunoglobulin hinge domain, including without limitation the human IgG4 hinge.

In some embodiments the transmembrane domain is CD28 transmembrane domain. In some embodiments the cytoplasmic co-stimulatory signaling domain is CD28 and/or 4-1BB. In some embodiment the construct further comprises T2A ribosomal skipping peptide, which can be used to link the CAR to a protein or peptide of interest, e.g. an epitope tag. In some embodiment a sortable tag is included, e.g. truncated epidermal growth factor receptor (EGFRt) or fluorescent proteins, which can be used to separate T cells expressing the CAR.

In some specific embodiments the linker joining the two scFv sequences is a rigid linker. In some specific embodiments, a rigid linker has the sequence SEQ ID NO:1 (EAAAK)n, where n is 1, 2, 3, 4, 5, 6, etc.. In some specific embodiments, n is 3.

In some embodiments the CAR construct is packaged into a lentiviral vector, which includes, without limitation, a third-generation lentiviral vector. Primary human T cells can be lentivirally transduced to stably integrate and express the OR-gate CAR. CAR-expressing cells can be enriched by fluorescence- or magnetism-activated cell sorting and expanded by antigen stimulation or stimulation with CD3/CD28 antibodies or antibody-coated microbeads.

In some embodiments of the invention, an expression vector encoding the CD19-or-CD20 CAR is provided, where the vector may be a lentiviral vector, a retroviral vector, an adenoviral vector, an adeno-associated viral vector, a plasmid, or RNA.

In some embodiments, a method of killing a cancer cell in an individual is provided, comprising the step of providing to the individual a therapeutically effective amount of a therapeutic cell of the invention, including an effector cell, such as a T cell, NK cell, NKT cell, etc., for example. The individual may have a B-cell malignancy, expressing on or both of CD20 and CD19. Any method of the invention may further comprise the step of delivering to the individual an additional cancer therapy, such as surgery, radiation, hormone therapy, chemotherapy, immunotherapy, or a combination thereof, for example.

In embodiments of the invention, a kit is provided comprising cells comprising a CD19-or-CD20 CAR and/or expression vector encoding a CD19-or-CD20 CAR.

BRIEF DESCRIPTION OF THE DRAWINGS

For a more complete understanding of the present invention, reference is now made to the following descriptions taken in conjunction with the accompanying drawing.

FIG. 1. Schematic of bispecific, CD20-OR-CD19 CAR. The bispecific CAR is composed of (from N to C terminal): A signal sequence that directs CAR localization to the cell membrane, the CD20 scFv, a peptide linker (e.g., (G4S)1 (SEQ ID NO: 15), (G4S)3 (SEQ ID NO: 16), SEQ ID NO:1 (EAAAK)1, or SEQ ID NO:17 (EAAAK)3), the CD19 scFv, followed by a spacer (e.g., the IgG4 hinge domain), a transmembrane domain (e.g., the transmembrane domain of CD28), one or more co-stimulatory domains (e.g., the cytoplasmic domain of 4-1BB or CD28), and the cytoplasmic domain of CD3 ξ chain. To facilitate identification of CAR-expressing T cells by antibody staining, truncated epidermal growth factor receptor (EGFRt) can be linked to the CAR via a self-cleaving peptide (e.g., T2A).

FIG. 3 discloses "(G4S)1" as SEQ ID NO: 15, "(G4S)4" as SEQ ID NO: 19, "(EAAAK)1" as SEQ ID NO: 1 and "(EAAAK)3" as SEQ ID NO: 17.

FIG. 4A-4B. Bispecificity is not compromised CD19 detection by OR-gate CARs. CAR-T cells were co-incubated with wildtype Raji or CD19+K562 targets for 24 hours. (A) CD69, CD137, and CD107a surface expression was quantified by flow cytometry. (B) IFN-γ, TNF-α, and IL-2 production was quantified by cytometric bead array assay. Reported values are the mean of triplicates, with error bars indicating one standard deviation. CAR identities are as described in FIG. 2.

FIG. 5 discloses "(G4S)4" as SEQ ID NO: 19 and "(EAAAK)3" as SEQ ID NO: 17).

FIG. 6 discloses "(EAAAK)3" as SEQ ID NO: 17).

DETAILED DESCRIPTION OF THE EMBODIMENTS

Figures 2A, 2B:
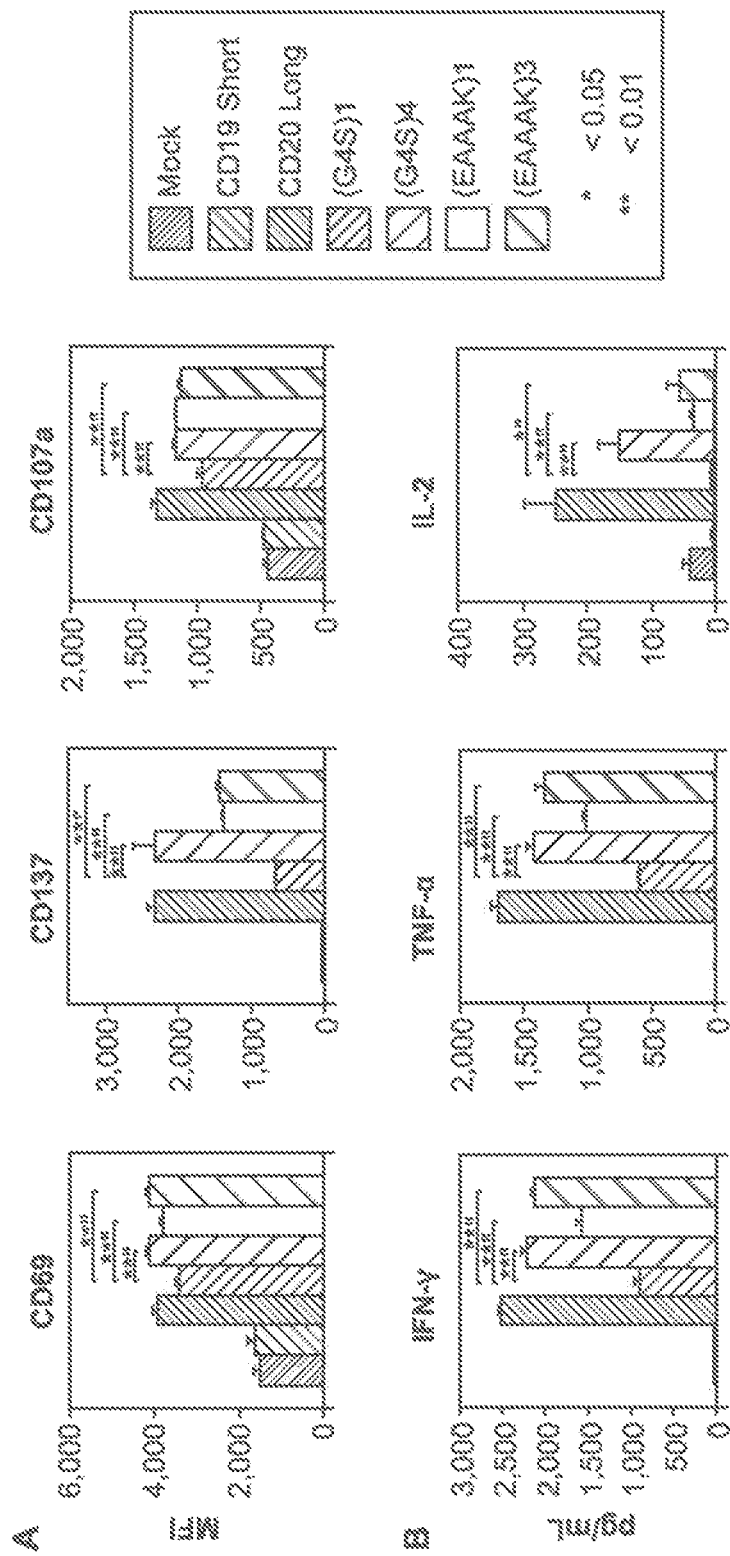
FIG. 2A-2B. OR-gate CARs but not single-input CD19 CARs respond to Raji lymphoma cells that have undergone antigen escape. (A) CD69, CD137, and CD107a surface expression (in median fluorescence intensity; MFI) by CAR-T cells after a 24-hour co-incubation with CD19-Raji cells. (B) IFN-γ, TNF-α, and IL-2 production by the CAR-T cells in (A) as measured by cytometric bead array assay. Mock: T cells that have been mock transduced and do not express CARs. CD19 Short: single-input CD19 CAR with IgG4 hinge as spacer. CD20 Long: single-input CD20 CAR with IgG4 hinge-CH2-CH3 as spacer. (G4S)1 (SEQ ID NO: 15), (G4S)4 (SEQ ID NO: 19), SEQ ID NO:1 (EAAAK)1, and SEQ ID NO:17 (EAAAK)3 indicate the linker sequence of CD20-OR-CD19 CARs, all of which contain the IgG4 hinge as spacer. Reported values are the mean of triplicates, with error bars indicating one standard deviation. P-values were calculated by two-tailed Student's t test; *: p<0.05; **: p<0.01.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

The term "genetic modification" means any process that adds, deletes, alters, or disrupts an endogenous nucleotide sequence and includes, but is not limited to viral mediated gene transfer, liposome mediated transfer, transformation, transfection and transduction, e.g., viral mediated gene transfer such as the use of vectors based on DNA viruses such as lentivirus, adenovirus, retroviruses, adeno-associated virus and herpes virus.

"Variant" refers to polypeptides having amino acid sequences that differ to some extent from a native sequence polypeptide. Ordinarily, amino acid sequence variants will possess at least about 80% sequence identity, more preferably, at least about 90% homologous by sequence. The amino acid sequence variants may possess substitutions, deletions, and/or insertions at certain positions within the reference amino acid sequence.

"Antibody-dependent cell-mediated cytotoxicity" and "ADCC" refer to a cell-mediated reaction in which nonspecific cytotoxic cells that express Fc receptors, such as natural killer cells, neutrophils, and macrophages, recognize bound antibody on a target cell and cause lysis of the target cell. ADCC activity may be assessed using methods, such as those described in U.S. Pat. No. 5,821,337.

"Effector cells" are leukocytes which express one or more constant region receptors and perform effector functions.

To "treat" a disease or a disorder, such as cancer, means to take either therapeutic measures or preventative measures to lessen or abate the disease or disorder. Such treatment includes prevention, alleviation of symptoms, diminishment or stabilization of scope, and/or remission.

The term "therapeutically effective amount" refers to an amount of a compound or molecule effective to treat a disease or disorder.

"Cancer" refers to cells undergoing uncontrolled cellular growth. Examples of cancer include colorectal cancer and head and neck cancer. A "chemotherapeutic agent" is a chemical compound useful in the treatment of cancer.

A "cytokine" is a protein released by one cell to act on another cell as an intercellular mediator.

"Non-immunogenic" refers to a material that does not initiate, provoke or enhance an immune response where the immune response includes the adaptive and/or innate immune responses.

The term "gene" means the segment of DNA involved in producing a polypeptide chain; it includes regions preceding and following the coding region "leader and trailer" as well as intervening sequences (introns) between individual coding segments (exons). Some genes may be developed which lack, in whole or in part, introns. Some leader sequences may enhance translation of the nucleic acid into polypeptides.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "vector" may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. Transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

"Receptor" means a polypeptide that is capable of specific binding to a molecule. Whereas many receptors may typically operate on the surface of a cell, some receptors may bind ligands when located inside the cell (and prior to transport to the surface) or may reside predominantly intracellularly and bind ligand therein.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments of antibodies, including e.g., Fab', F(ab')$_2$, Fab, Fv, rIgG, and scFv fragments. The term scFv refers to a single chain Fv antibody in which the variable domains of the heavy chain and of the light chain of a traditional two chain antibody have been joined to form one chain.

The use of a single chain variable fragment (scFv) is of particular interest. scFvs are recombinant molecules in which the variable regions of light and heavy immunoglobulin chains encoding antigen-binding domains are engineered into a single polypeptide. Generally, the $V_H$ and $V_L$ sequences are joined by a linker sequence. See, for example, Ahmad (2012) Clinical and Developmental Immunology Article ID 980250, herein specifically incorporated by reference.

The length of the DNA linker used to link both of the domains is important for proper folding. It has been estimated that the peptide linker must span 3.5 nm (35 Å) between the carboxy terminus of the variable domain and the amino terminus of the other domain without affecting the ability of the domains to fold and form an intact antigen-binding site. Many such linkers are known in the art, for example flexible linkers comprising stretches of Gly and Ser residues. The linkers used in the present invention include, without limitation, a rigid linker. In some specific embodiments of the invention, a rigid linker has the sequence SEQ ID NO: 1 (EAAAK)n, where n is 1, 2, 3, 4, 5, 6, etc. In some specific embodiments, n is 3.

Spacer. A spacer region links the antigen binding domain to the transmembrane domain. It should be flexible enough to allow the antigen binding domain to orient in different directions to facilitate antigen recognition. The simplest form is the hinge region from an immunoglobulin, e.g. the hinge from any one of IgG1, IgG2a, IgG2b, IgG3, IgG4, particularly the human protein sequences. Alternatives include the $CH_2CH_3$ region of immunoglobulin and portions of CD3. For many scFv based constructs, an IgG hinge is effective.

T2A peptide. T2A peptide can be used to link the CAR of the invention to an epitope tag or other protein or peptide, including without limitation a sortable tag. T2A-linked multicistronic vectors can be used to express multiple proteins from a single open reading frame. The small T2A peptide sequences, when cloned between genes, allow for efficient, stoichiometric production of discrete protein products within a single vector through a novel "cleavage" event within the T2A peptide sequence. Various 2A peptide sequences are known and used in the art, for example see Szymczak-Workman et al. (2012) Cold Spring Harb Protoc. 2012(2):199-204, herein specifically incorporated by reference. They are small (18-22 amino acids) and have divergent amino-terminal sequences, which minimizes the chance for homologous recombination and allows for multiple, different 2A peptide sequences to be used within a single vector.

As used herein, the term "tumor microenvironment" refers to any and all elements of the tumor milieu that creates a structural and or functional environment for the malignant process to survive and/or expand and/or spread.

CD20 is a cell surface protein present on most B-cell neoplasms, and absent on otherwise similar appearing T-cell neoplasms. CD20 positive cells are also sometimes found in cases of Hodgkins disease, myeloma, and thymoma. CD20 is the target of the monoclonal antibodies (mAb) rituximab, ofatumumab, ocrelizumab, genmab, obinutuzumab, Ibritumomab tiuxetan, AME-133v, IMMU-106, TRU-015, and tositumomab, which are all active agents in the treatment of all B cell lymphomas and leukemias. For the purposes of the present invention, any of these antibodies may be converted into a scFv and used in the CAR. In some embodiments, the scFv is derived from Leu16 monoclonal antibody.

Cancers that may be treated with anti-CD20 reagents, e.g. antibodies and CARs, include without limitation B-cell lymphomas and leukemias, for example B-cell non-Hodgkin lymphomas (NHL), e.g. follicular lymphoma; hairy cell leukemia, and B-cell chronic lymphocytic leukemia (CLL). Anti-CD20 reagents are also useful in treating melanoma, e.g. targeting melanoma cancer stem cells.

CD19 expression is a hallmark of B cells. CD19 antigen is a type I transmembrane glycoprotein belonging to the immunoglobulin Ig superfamily. CD19 is specifically expressed in normal B cells and neoplastic B cells. It is considered a pan B-cell marker expressed throughout B-cell development but with threefold higher expression in mature cells as compared to immature B cells. CD19 expression however, is lost in the terminally differentiated plasma cells. During lymphopoiesis, CD19 directs B-cell fate and differentiation by modulating B-cell receptor signaling. It is critically involved in establishing the optimal immune response through its roles in the antigen-independent development as well as the immunoglobulin-induced activation of B cells. CD19 deficiency in humans and mice leads to an overall impaired humoral response with increased susceptibility to infection.

The pattern of CD19 expression is maintained among B-cell malignancies where it is expressed in indolent and aggressive subtypes of B cell lymphomas and leukemias, including NHL, B-cell CLL, and non-T acute lymphoblastic leukemia (ALL). CD19 is expressed in the B-cell lineage at an earlier stage compared with CD20. This fact therefore, may provide an advantage to CD19 targeted drugs over rituximab, especially for early B-cell neoplasms like acute lymphoblastic leukemia. Moreover, CD19 is shown to be internalized efficiently in lymphoma tumor models with the use of different monoclonal antibodies (huB4, hBU12). Various anti-CD19 antibodies can be formatted for use in the constructs of the present invention, including without limitation huB4, which is a humanized anti-CD19 antibody. In some embodiments of the invention, the anti-CD19 scFv is the FMC63 antibody.

Highly selective targeted T cell therapies are emerging as effective non-toxic modalities for the treatment of cancer. Malignancies are complex diseases where multiple elements contribute to the overall pathogenesis through both distinct and redundant mechanisms. Hence, targeting different cancer-specific markers simultaneously could result in better therapeutic efficacy. However, developing two separate cellular products for clinical use as combination therapy is impractical, owing to regulatory hurdles and cost. In contrast, rendering an individual T cell bispecific offsets tumor escape because of antigen loss.

In one embodiment, the bispecific CAR comprises a modified endogenous cell-surface molecule that may be used as a non-immunogenic selection epitope compatible with immunomagnetic selection. Non-immunogenic epitopes are those that normally do not raise an immune response in humans, and are usually proteins normally expressed in humans, or fragments thereof. Such a non-immunogenic selection epitope may facilitate immunotherapy in cancer patients without undesirable immunologic rejection of cell products. The endogenous cell surface molecule may be modified or truncated to retain an extracellular epitope recognized by a known antibody or functional fragment thereof, and to remove any signaling or trafficking domains and/or any extracellular domains unrecognized by said known antibody. A modified endogenous cell surface molecule which lacks a signaling or trafficking domain and/or any extracellular domains unrecognized by said known antibody is rendered inert. In some embodiments a truncated EGFR is used for this purpose.

The modified endogenous cell-surface molecule may be, but is not limited to, any non-immunogenic cell-surface related receptor, glycoprotein, cell adhesion molecule, antigen, integrin or cluster of differentiation (CD) that is modified as described herein. Modification of such cell-surface molecules is accomplished by keeping an epitope that is recognized by a known antibody or functional fragment thereof; and removing any signaling or trafficking domains and/or any extracellular domains unrecognized by a known antibody. Removal of the signaling or trafficking domains and/or any extracellular domains unrecognized by a known antibody renders the endogenous cell-surface molecule non-immunogenic and/or inert.

Thus, embodiments of the invention utilize an OR gate CAR as an artificial molecule that enables immune cells (T cells) to specifically and distinctly recognize and attack two cancer target molecules simultaneously, or to attack a cancer cell that has lost expression of either CD20 or CD19. The CAR is an artificial molecule that can be grafted onto T cells using genetic engineering technology to render them specific to a target of interest. This ability has substantial therapeutic implications, in that escape from single activity CARs has been reported.

The CAR architecture may be any suitable architecture, as known in the art. In certain embodiments, a cytoplasmic signaling domain, such as those derived from the T cell receptor ξ-chain, is employed as at least part of the chimeric receptor in order to produce stimulatory signals for T lymphocyte proliferation and effector function following engagement of the chimeric receptor with the target antigen. Examples would include, but are not limited to, endodomains from co-stimulatory molecules such as CD28, 4-11BB, and OX40 or the signaling components of cytokine receptors such as IL7 and IL15. In particular embodiments, co-stimulatory molecules are employed to enhance the activation, proliferation, and cytotoxicity of T cells produced by the CAR after antigen engagement. In specific embodiments, the co-stimulatory molecules are CD28, OX40, and 4-1BB and cytokine and the cytokine receptors are IL7 and IL15. The CAR may be first generation, second generation, or third generation CAR, in which signaling is provided by CD3ξ together with co-stimulation provided by CD28 and a tumor necrosis factor receptor (TNFr), such as 4-1BB or OX40), for example.

Embodiments of the invention include cells that express an OR-gate CAR of the invention. The cell may be of any kind, including an immune cell capable of expressing the OR-gate CAR of the invention for cancer therapy or a cell, such as a bacterial cell, that harbors an expression vector that encodes the OR-gate CAR of the invention. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T cells or killer T cell); NK cells and NKT cells are also encompassed in the invention.

The cells can be autologous cells, syngeneic cells, allogeneic cells and even in some cases, xenogeneic cells. In many situations one may wish to be able to kill the modified CTLs, where one wishes to terminate the treatment, the cells become neoplastic, in research where the absence of the cells after their presence is of interest, or other event. For this purpose one can provide for the expression of certain gene products in which one can kill the modified cells under controlled conditions, such as inducible suicide genes.

By way of illustration, cancer patients or patients susceptible to cancer or suspected of having cancer may be treated as follows. Cancers include particularly B-cell leukemias and lymphomas. CTLs modified as described herein may be administered to the patient and retained for extended periods of time. The individual may receive one or more administrations of the cells. In some embodiments, the genetically modified cells are encapsulated to inhibit immune recognition and placed at the site of the tumor. The cells may be injected at the tumor site or injected intravenously, for example.

In particular cases the individual is provided with therapeutic CTLs modified to comprise an OR-gate CAR of the invention. The cells may be delivered at the same time or at different times as another type of cancer therapy. The cells may be delivered in the same or separate formulations as another type of cancer therapy. The cells may be provided to the individual in separate delivery routes as another type of cancer therapy. The cells may be delivered by injection at a tumor site or intravenously or orally, for example. Routine delivery routes for such compositions are known in the art.

Expression vectors that encode the OR-gate CAR of the invention can be introduced as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example, one can knock-out an endogenous gene and replace it (at the same locus or elsewhere) with the gene encoded for by the construct using materials and methods as are known in the art for homologous recombination. For homologous recombination, one may use either omega or O-vectors. Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

The CTLs that have been modified with the construct(s) are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, including humans, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The cells may be administered as desired. Depending upon the response desired, the manner of administration, the life of the cells, the number of cells present, various protocols may be employed. The number of administrations will depend upon the factors described above at least in part.

In some embodiments AAV, retroviral or lentiviral vectors are used to deliver the OR-gate CAR of the invention to a T cell.

Adeno associated virus (AAV) is an attractive vector system for use in the cells of the present invention as it has a high frequency of integration and it can infect nondividing cells, thus making it useful for delivery of genes into mammalian cells, for example, in tissue culture or in vivo. AAV has a broad host range for infectivity. Details concerning the generation and use of rAAV vectors are described in U.S. Pat. Nos. 5,139,941 and 4,797,368, each incorporated herein by reference.

Retroviruses are useful as delivery vectors because of their ability to integrate their genes into the host genome, transferring a large amount of foreign genetic material, infecting a broad spectrum of species and cell types and of being packaged in special cell lines.

Lentiviruses are complex retroviruses, which, in addition to the common retroviral genes gag, pol, and env, contain other genes with regulatory or structural function.

Lentiviral vectors are well known in the art. Some examples of lentivirus include the Human Immunodeficiency Viruses: HIV-1, HIV-2 and the Simian Immunodeficiency Virus: SIV. Recombinant lentiviral vectors are capable of infecting non-dividing cells and can be used for both in vivo and ex vivo gene transfer and expression of nucleic acid sequences. In some embodiments the lentiviral vector is a third generation vector (see, for example, Dull et al. (1998) J Virol. 72(11):8463-71). Such vectors are commercially available. 2nd generation lentiviral plasmids utilize the viral LTR promoter for gene expression, whereas 3rd-generation transfer vectors utilize a hybrid LTR promoter, see, for example Addgene for suitable vectors.

Any of the compositions described herein may be comprised in a kit. In a non-limiting example, one or more cells for use in cell therapy and/or the reagents to generate one or more cells for use in cell therapy that harbors recombinant expression vectors may be comprised in a kit. The kit components are provided in suitable container means. Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Cancer therapies also include a variety of combination therapies with both chemical and radiation based treatments. Combination chemotherapies include, for example, Abraxane®, Altretamine®, docetaxel, Herceptin®, methotrexate, Novantrone™, Zoladex™, cisplatin (CDDP), Carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16™), tamoxifen, raloxifene, estrogen receptor binding agents, Taxol®, gemcitabien, Navelbine®, farnesyl-protein tansferase inhibitors, transplatinum, 5-fluorouracil, vincristin, vinblastin and methotrexate, or any analog or derivative variant of the foregoing and also combinations thereof.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

All references cited in this specification are hereby incorporated by reference in their entirety. The following examples are solely for the purpose of illustrating one embodiment of the invention.

EXPERIMENTAL

Bispecific CD20-or-CD19 CAR

A bispecific CAR was constructed to have, from N to C terminal, a signal sequence that directs CAR localization to the cell membrane, the CD20 scFv, a peptide linker, the CD19 scFv, followed by a spacer (e.g., the IgG4 hinge domain), a transmembrane domain (e.g., the transmembrane domain of CD28), none or one or more co-stimulatory domains (e.g., the cytoplasmic domain of 4-1BB or CD28), and the cytoplasmic domain of CD3 ξ chain. To facilitate identification of CAR-expressing T cells by antibody staining, truncated epidermal growth factor receptor (EGFRt) can be linked to the CAR via a self-cleaving peptide (e.g., T2A).

The amino acid sequence of various components is as follows:

```
GMpCSF signal sequence,
                                         (SEQ ID NO: 2)
METDTLLLWVLLLWVPGSTG CD20 scFv
                                         (SEQ ID NO: 3)
DIVLTQSPAILSASPGEKVTMTCRASSSVNYMDWYQKKPGSSPKP

WIYATSNLASGVPARFSGSGSGTSYSLTISRVEAEDAATYYCQQW

SFNPPTFGGGTKLEIKGSTSGGGSGGGSGGGGSSEVQLQQSGAEL

VKPGASVKMSCKASGYTFTSYNMHWVKQTPGQGLEWIGAIYPGNG

DTSYNQKFKGKATLTADKSSSTAYMQLSSLTSEDSADYYCARSNY

YGSSYWFFDVWGAGTTVTVSS

CD19 scFv
                                         (SEQ ID NO: 4)
DIQMTQTTSSLSASLGDRVTISCRASQDISKYLNWYQQKPDGTVK

LLIYHTSRLHSGVPSRFSGSGSGTDYSLTISNLEQEDIATYFCQQ

GNTLPYTFGGGTKLEITGSTSGSGKPGSGEGSTKGEVKLQESGPG

LVAPSQSLSVTCTVSGVSLPDYGVSWIRQPPRKGLEWLGVIWGSE

TTYYNSALKSRLTIIKDNSKSQVFLKMNSLQTDDTAIYYCAKHYY

YGGSYAMDYWGQGTSVTVSS

IgG4 Hinge
                                         (SEQ ID NO: 5)
ESKYGPPCPPCP

CD28 transmembrane domain
                                         (SEQ ID NO: 6)
MFWVLVVVGGVLACYSLLVTVAFIIFWV CD28 cytoplasmic domain
                                         (SEQ ID NO: 7)
RSKRSRGGHSDYMNMTPRRPGPTRKHYQPYAPPRDFAAYRS 4-1BB cytoplasmic domain
                                         (SEQ OD NO: 8)
KRGRKKLLYIFKQPFMRPVQTTQEEDGCSCRFPEEEEGGCEL CD3z cytoplasmic domain
                                         (SEQ ID NO: 9)
RVKFSRSADAPAYQQGQNQLYNELNLGRREEYDVLDKRRGRDPEM

GGKPRRKNPQEGLYNELQKDKMAEAYSEIGMKGERRRGKGHDGLY

QGLSTATKDTYDALHMQALPPR

T2A self-cleaving peptide
                                         (SEQ ID NO: 10)
LEGGGEGRGSLLTCGDVEENPGPR IgG4 CH2
                                         (SEQ ID NO: 11)
APEFLGGPSVFLFPPKPKDTLMISRTPEVTCVVVDVSQEDPEVQF

NWYVDGVEVHNAKTKPREEQFNSTYRVVSVLTVLHQDWLNGKEYK

CKVSNKGLPSSIEKTISKAK

IgG4 CH3
                                         (SEQ ID NO: 12)
GQPREPQVYTLPPSQEEMTKNQVSLTCLVKGFYPSDIAVEWESNG

QPENNYKTTPPVLDSDGSFFLYSRLTVDKSRWQEGNVFSCSVMHE

ALHNHYTQKSLSLSLGK

Truncated epidermal growth factor
receptor (EGFRt)
                                         (SEQ ID NO: 13)
MLLLVTSLLLCELPHPAFLLIPRKVCNGIGIGEFKDSLSINATNI

KHFKNCTSISGDLHILPVAFRGDSFTHTPPLDPQELDILKTVKEI

TGFLLIQAWPENRTDLHAFENLEIIRGRTKQHGQFSLAVVSLNIT

SLGLRSLKEISDGDVIISGNKNLCYANTINWKKLFGTSGQKTKII

SNRGENSCKATGQVCHALCSPEGCWGPEPRDCVSCRNVSRGRECV

DKCNLLEGEPREFVENSECIQCHPECLPQAMNITCTGRGPDNCIQ

CAHYIDGPHCVKTCPAGVMGENNTLVWKYADAGHVCHLCHPNCTY

GCTGPGLEGCPTNGPKIPSIATGMVGALLLLLVVALGIGLFM
```

OR-gate CARs but not single-input CD19 CARs respond to Raji lymphoma cells that have undergone antigen escape, as shown in FIG. 2 by expression of CD69, CD137 and CD1-7a on the surface of the CAR-expressing T cells, and by the release of cytokines. The controls include a CD19 Short single-input CD19 CAR with IgG4 hinge as spacer; and CD20 Long single-input CD20 CAR with IgG4 hinge-CH2-CH3 as spacer. Various linkers were tested, including (G4S)1 (SEQ ID NO: 15), (G4S)4 (SEQ ID NO: 19), (SEQ ID NO:1, EAAAK)1, and (SEQ ID NO:17, EAAAAK)3.

Figure 3:
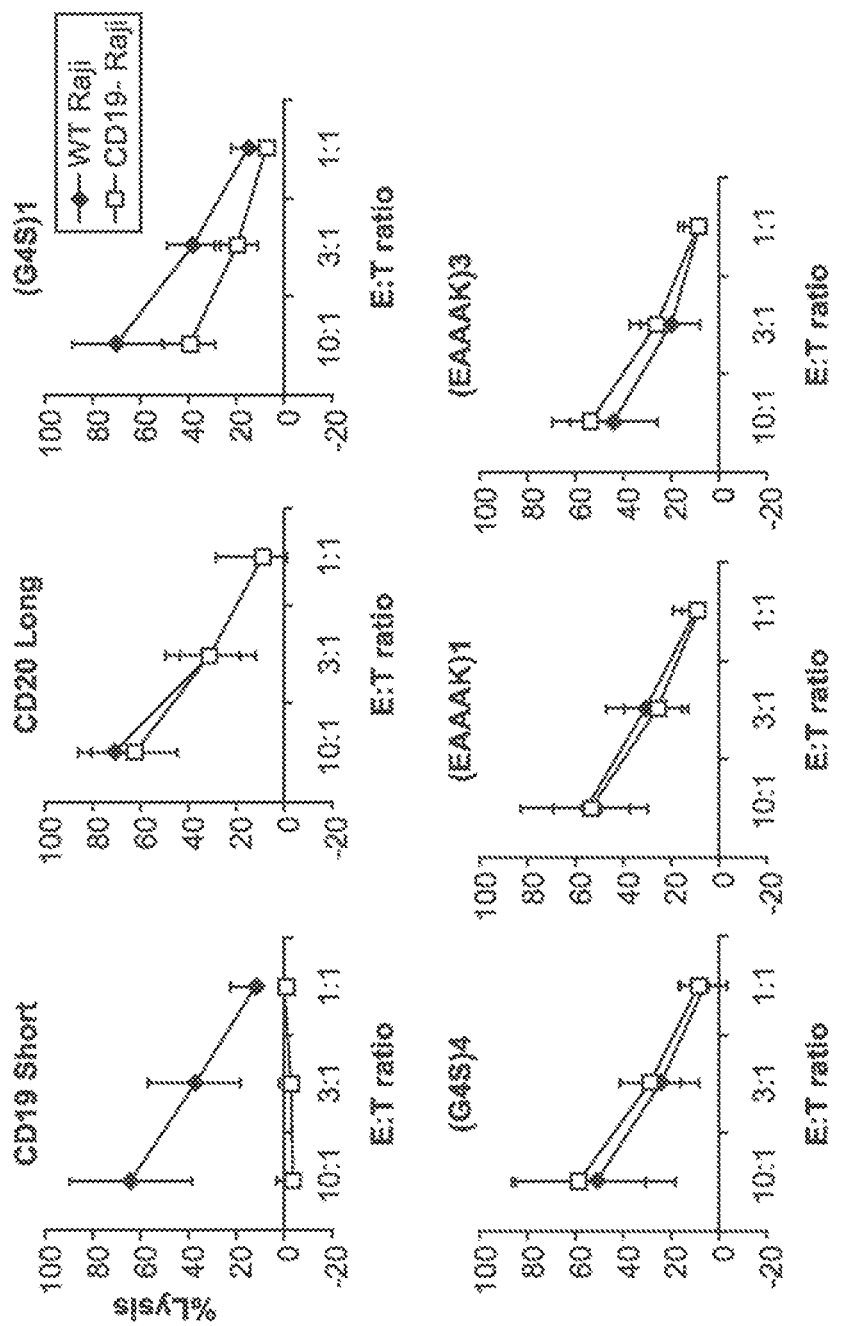
FIG. 3. Cell lysis by single-input and OR-gate CAR-T cells after 4-hour co-incubation with wildtype (WT; CD19+/CD20+) or CD19-Raji (CD19-/CD20+) cells. Reported values are the mean of triplicates, with error bars indicating one standard deviation. CAR identities are as described in FIG. 2.
Figure 4:
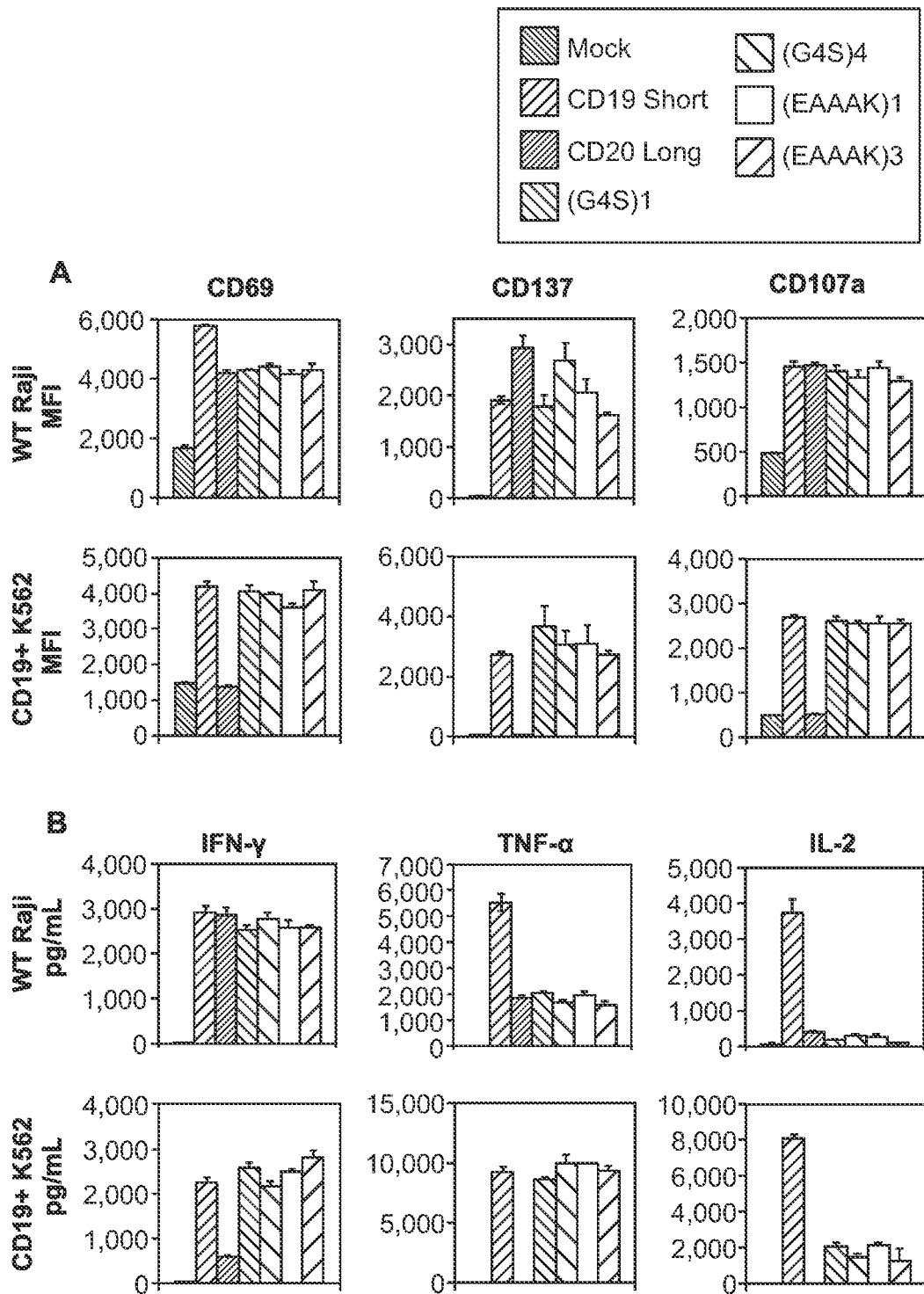
FIG. 4 discloses "(G4S)1" as SEQ ID NO: 15, "(G4S)4" as SEQ ID NO: 19, "(EAAAK)1" as SEQ ID NO: 1 and "(EAAAK)3" as SEQ ID NO: 17.

A comparison of cell lysis by single-input and OR-gate CAR-T cells after 4-hour co-incubation with wildtype (WT; CD19+/CD20+) or CD19-Raji (CD19−/CD20+) cells is shown in FIG. 3. The bispecificity was not compromised in OR-gate CARs. CAR-T cells were co-incubated with WT Raji or CD19+K562 targets for 24 hours, and the expression of relevant activation-induced antigens and release of cytokines are shown in FIG. 4.

Figures 5A, 5B, 5C, 5D, 5E:
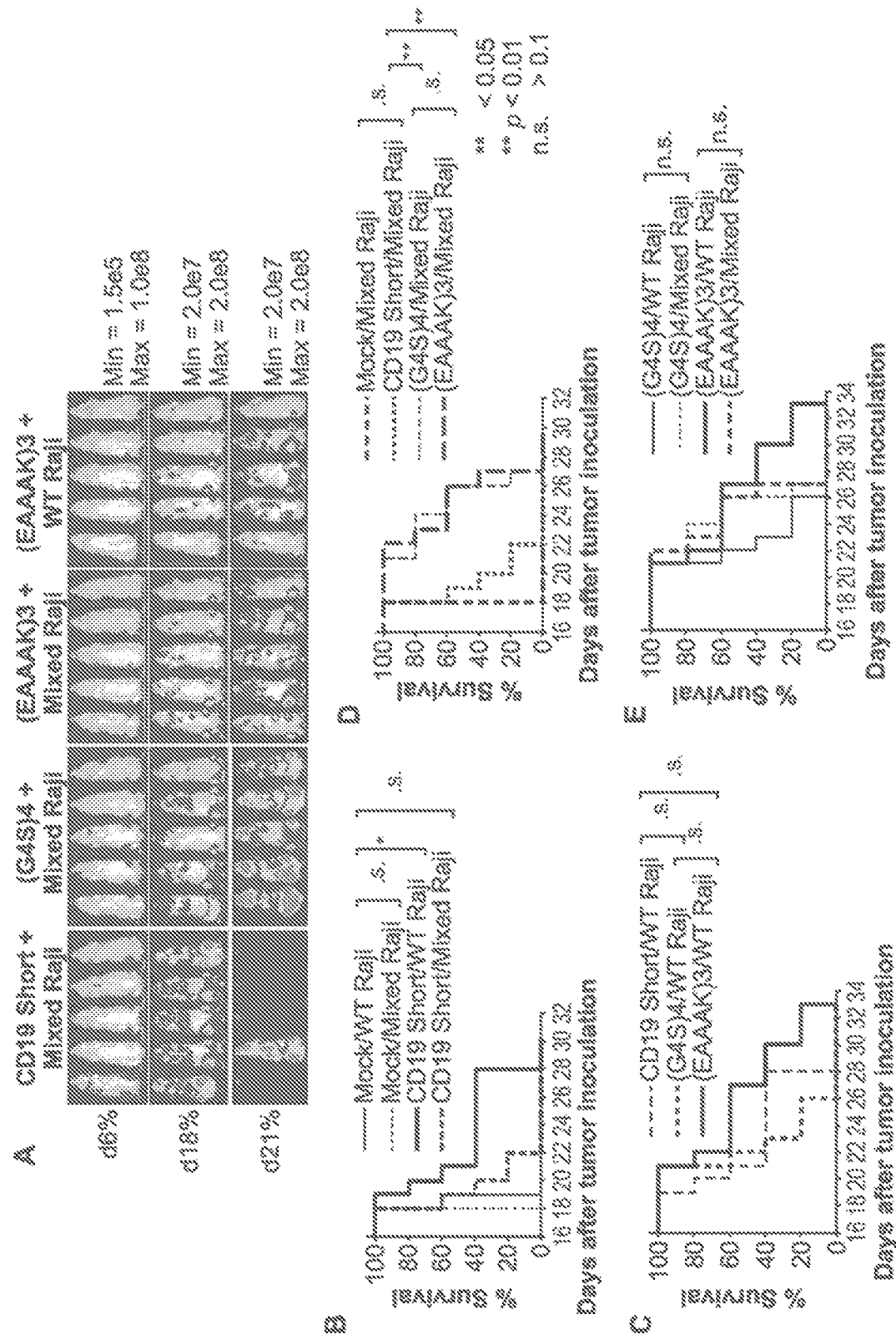
FIG. 5A-5E. OR-gate CARs abrogate the effects of antigen escape in vivo. (A) Tumor progression in NSG mice bearing wildtype (WT) or mixed (75% wildtype; 25% CD19-) Raji xenografts. Bioluminescence imaging was performed on days 6, 18, and 21 post tumor injection (T cells were injected on day 7). (B) Survival of mice bearing WT or mixed Raji tumor xenografts and treated with T cells expressing no CAR or the single-input CD19 CAR. Results indicate single-input CD19 CAR is able to significantly extend the survival of animals engrafted with WT Raji tumors. (C) Survival of mice bearing WT Raji tumor xenografts and treated with T cells expressing the single-input CD19 CAR or OR-gate CARs. Results indicate OR-gate CARs are as efficient as single-input CD19 CAR in targeting wildtype Raji lymphoma. (D) Survival of mice bearing mixed Raji tumor xenografts and treated with T cells expressing no CAR, the single-input CD19 CAR, or OR-gate CARs. Results indicate only OR-gate CARs are able to significantly extend survival of animals bearing CD19-mutant tumors. (E) Survival of mice bearing WT or mixed Raji tumor xenografts and treated with T cells expressing OR-gate CARs. Results indicate OR-gate CARs are equally efficient against WT and CD19-mutant Raji tumors, thus rendering the T cells insensitive to antigen loss by target cells. N=5 in all test groups. P-values were calculated by log-rank test analysis; n.s.: not significant (p>0.1); *: p<0.1; **: p<0.05. CAR identities are as described in FIG. 2.
Figure 6:
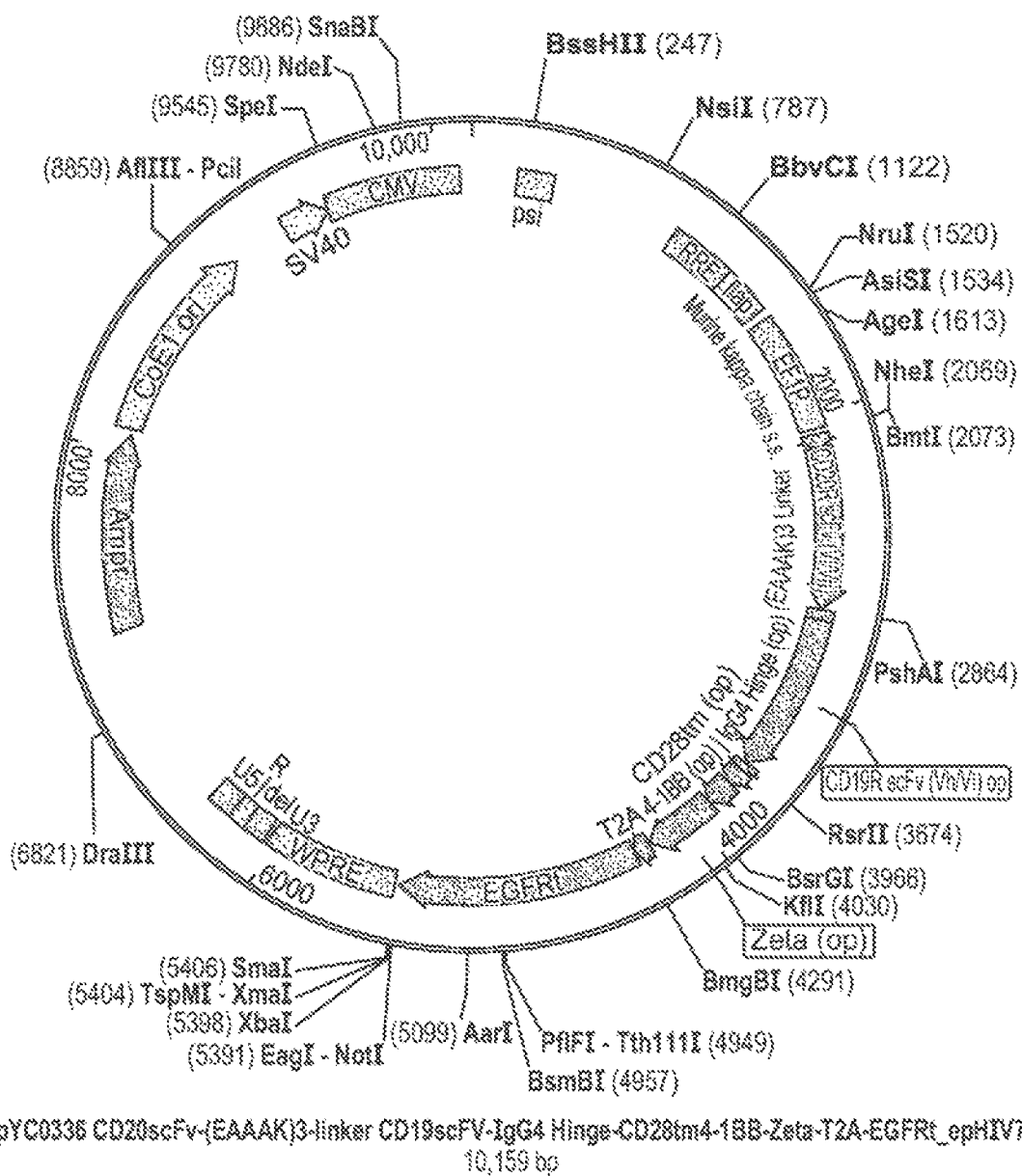
FIG. 6. Representative plasmid map of a bispecific, CD20-OR-CD19 CAR.

In vivo data, shown in FIG. 5, show OR-gate CARs abrogate the effects of antigen escape. In the survival of mice bearing WT or mixed Raji tumor xenografts and treated with T cells expressing no CAR or the single-input CD19 CAR, the results showed that single-input CD19 CAR was able to significantly extend the survival of animals engrafted with WT Raji tumors, and that OR-gate CARs are as efficient as single-input CD19 CAR in targeting WT Raji lymphoma. However, only OR-gate CARs were able to significantly extend survival of animals bearing CD19-mutant tumors. OR-gate CARs are equally efficient against WT and CD19-mutant Raji tumors, thus rendering the T cells insensitive to antigen loss by target cells.

What is claimed is:

1. A polypeptide comprising a CD19-OR-CD20 chimeric antigen receptor (CAR), wherein the CAR comprises from N- to C-terminus:
   a) an anti-CD20 scFv comprising a variable light domain and a variable heavy domain obtained from ofatumumab;
   b) a $(G_4S)_n$ linker, wherein n is 1 (SEQ ID NO: 15), 3 (SEQ ID NO: 16), or 4 (SEQ ID NO: 19);
   c) an anti-CD19 scFv comprising a variable heavy domain and a variable light domain from a sequence of SEQ ID NO:4;
   d) a spacer of SEQ ID NO:5;
   e) a transmembrane domain of SEQ ID NO:6;
   f) a co-stimulatory domain of SEQ ID NO:8; and
   g) a CD3-zeta cytoplasmic signaling domain of SEQ ID NO:9.

2. The polypeptide of claim 1, wherein the $(G_4S)_n$ linker is $(G_4S)_1$ (SEQ ID NO: 15).

3. The polypeptide of claim 1, wherein the $(G_4S)_n$ linker is $(G_4S)_3$ (SEQ ID NO: 16).

4. The polypeptide of claim 1, wherein the $(G_4S)_n$ linker is $(G_4S)_4$ (SEQ ID NO: 19).

5. A nucleic acid encoding the polypeptide of claim 1.

6. A viral vector comprising the nucleic acid of claim 5.

7. The viral vector of claim 6, wherein the vector is a lentiviral vector.

8. A cell comprising the polypeptide of claim 1.

9. The cell of claim 8, wherein the cell is a T cell, a NK cell, or a NKT cell.

* * * * *